United States Patent
Allen et al.

(10) Patent No.: US 9,549,882 B2
(45) Date of Patent: *Jan. 24, 2017

(54) GEL VOLUME MASCARA

(71) Applicant: Coty Inc., New York, NY (US)

(72) Inventors: Nykol Allen, New York, NY (US); Julianne Sortino, New York, NY (US)

(73) Assignee: Coty Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,328

(22) Filed: Jan. 25, 2016

(65) Prior Publication Data

US 2016/0136061 A1   May 19, 2016

Related U.S. Application Data

(63) Continuation of application No. 14/462,055, filed on Aug. 18, 2014, now Pat. No. 9,241,892.

(60) Provisional application No. 61/868,206, filed on Aug. 21, 2013.

(51) Int. Cl.

| | |
|---|---|
| A61K 8/04 | (2006.01) |
| A61K 8/92 | (2006.01) |
| A61Q 1/10 | (2006.01) |
| A61K 8/19 | (2006.01) |
| A61K 8/25 | (2006.01) |
| A61K 8/36 | (2006.01) |
| A61K 8/34 | (2006.01) |
| A61K 8/31 | (2006.01) |
| A61K 8/44 | (2006.01) |
| A61K 8/55 | (2006.01) |
| A61K 8/58 | (2006.01) |
| A61K 8/81 | (2006.01) |
| A61K 8/86 | (2006.01) |
| A61K 8/88 | (2006.01) |
| A61K 8/37 | (2006.01) |
| A61K 8/49 | (2006.01) |

(52) U.S. Cl.
CPC ............ *A61K 8/042* (2013.01); *A61K 8/19* (2013.01); *A61K 8/25* (2013.01); *A61K 8/31* (2013.01); *A61K 8/34* (2013.01); *A61K 8/345* (2013.01); *A61K 8/361* (2013.01); *A61K 8/37* (2013.01); *A61K 8/44* (2013.01); *A61K 8/4993* (2013.01); *A61K 8/55* (2013.01); *A61K 8/585* (2013.01); *A61K 8/8147* (2013.01); *A61K 8/86* (2013.01); *A61K 8/88* (2013.01); *A61K 8/92* (2013.01); *A61K 8/922* (2013.01); *A61K 8/927* (2013.01); *A61Q 1/10* (2013.01)

(58) Field of Classification Search
None
See application file for complete search history.

(56) References Cited

U.S. PATENT DOCUMENTS

| | | | |
|---|---|---|---|
| 5,356,627 A | 10/1994 | Da Cunha et al. | |
| 5,534,247 A * | 7/1996 | Franjac | A61K 8/06 132/218 |
| 5,800,825 A | 9/1998 | Mcmullen | |
| 9,241,892 B2 | 1/2016 | Allen et al. | |
| 2004/0122152 A1 | 6/2004 | Sengupta et al. | |
| 2005/0042191 A1 | 2/2005 | Travkina et al. | |
| 2006/0171913 A1 | 8/2006 | Schroder | |
| 2008/0119570 A1 | 5/2008 | Brieva et al. | |
| 2009/0035335 A1 | 2/2009 | Marotta et al. | |
| 2012/0308504 A1 | 12/2012 | Andréo et al. | |
| 2013/0164241 A1 | 6/2013 | Foley et al. | |
| 2015/0056153 A1 | 2/2015 | Allen et al. | |

FOREIGN PATENT DOCUMENTS

| | | |
|---|---|---|
| JP | 08-506342 A | 7/1996 |
| JP | 2001-506608 A | 5/2001 |
| JP | 2003-128522 A | 5/2003 |
| JP | 2004-529985 A | 9/2004 |
| JP | 2006-519686 A | 8/2006 |
| JP | 2010-535224 A | 11/2010 |
| WO | WO-9417775 A1 | 8/1994 |
| WO | WO-2009018064 A2 | 2/2009 |
| WO | WO-2015026721 A1 | 2/2015 |

OTHER PUBLICATIONS

"U.S. Appl. No. 14/462,055, Notice of Allowance mailed Nov. 25, 2015", 7 pgs.
"International Application Serial No. PCT/US2014/051493, International Search Report mailed Nov. 18, 2014", 3 pgs.
"International Application Serial No. PCT/US2014/051493, Written Opinion mailed Nov. 18, 2014", 5 pgs.
"Canadian Application Serial No. 2,920,115, Office Action mailed Mar. 16, 2016", 4 pgs.
"European Application Serial No. 14837654.4, Extended European Search Report mailed Apr. 5, 2016", 10 pgs.
"Canadian Application Serial No. 2,920,115, Office Action mailed Oct. 6, 2016", 3 pgs.
"Canadian Application Serial No. 2,920,115, Response filed Sep. 15, 2016 to Office Action mailed Mar. 16, 2016", 30 pgs.
"European Application Serial No. 14837654.4, Response filed Oct. 27, 2016 to Extended European Search Report mailed Apr. 5, 2016," 11 pgs.
"Japanese Application Serial No. 2016-516052, Office Action mailed Sep. 6, 2016", (w/ English Translation), 18 pgs.

* cited by examiner

*Primary Examiner* — Robert A Wax
*Assistant Examiner* — Melissa Mercier
(74) *Attorney, Agent, or Firm* — Schwegman Lundberg & Woessner, P.A.

(57) ABSTRACT

Inventive embodiments disclosed herein relate to gel volume mascara. The mascara includes water in a concentration of at least about 45% by weight; disodium ethylenediaminetetraacetate; Polysorbate 20; Black iron oxide; One or more waxes selected from the group consisting of beeswax, Cera Carnauba/*Copernicia Cerifera* (Carnauba) Wax/CIRE de Carnauba, and paraffin in a concentration of 15-20% by weight; and a synthetic layered silicate, insoluble in water, in a concentration effective for forming a colloidal dispersion with the water.

7 Claims, No Drawings

GEL VOLUME MASCARA

FIELD

Inventive embodiments disclosed herein relate to gel volume mascara.

BACKGROUND

The ancient Egyptians believed that the eyes were windows to the soul and that it was important to conceal them from evil spirits with eye liner and mascara. The first mascara was made of ingredients that included kohl, crocodile dung, water and honey. This mascara was applied with bone and ivory applicators.

In 1913, Eugene Rimmel created the first mass produced non-toxic mascara, not to drive away evil spirits but impart length and volume to eyelashes. The Rimmel mascara was made from a mixture of petroleum and black coal dust.

SUMMARY

One inventive embodiment disclosed herein includes mascara. The mascara includes the following ingredients in the following concentrations:

| Ingredient | % w/w |
|---|---|
| Water | 53.70000 |
| Iron Oxides | 10.00000 |
| Beeswax | 7.00000 |
| Cera Carnauba/*Copernicia Cerifera* (Carnauba) Wax/CIRE de Carnauba | 6.00000 |
| Paraffin | 4.80000 |
| Polysorbate 20 | 2.42500 |
| Water | 2.41000 |
| *Euphorbia Cerifera* (Candelilla) Wax | 2.00000 |
| Nylon-6/12 | 2.00000 |
| Lithium Magnesium Sodium Silicate | 1.50000 |
| Potassium Cetyl Phosphate | 1.27500 |
| Hydrogenated Palm Glycerides | 1.22500 |
| Ammonium Acrylates Copolymer | 1.17300 |
| Trimethylsiloxysilicate | 1.00000 |
| Cyclopentasiloxane | 1.00000 |
| Stearic Acid | 1.00000 |
| Phenoxyethanol | 0.80910 |
| Alcohol Denat. | 0.22500 |
| Disodium Deceth-5 Sulfosuccinate | 0.12000 |
| Sodium Hydroxide | 0.10000 |
| Ethylhexyl glycerin | 0.09000 |
| Disodium EDTA | 0.09000 |
| Laureth-30 | 0.04500 |
| Sodium Dehydroacetate | 0.01200 |
| Tocopheral | 0.00090 |

Another embodiment includes a mascara that includes the following ingredients: Water in a concentration of at least about 45% by weight;
  Disodium ethylenediaminetetraacetate;
  Polysorbate 20;
  Black iron oxide;
  One or more waxes selected from the group consisting of beeswax, Cera Carnauba/*Copernicia Cerifera* (Carnauba) Wax/CIRE de Carnauba, and paraffin in a concentration of 15-20% by weight; and
  A synthetic layered silicate, insoluble in water, in a concentration effective for forming a colloidal dispersion with the water.

Another embodiment includes a method of making a gel volume mascara. The method includes preparing a first phase of deionized water and ethylenediaminetetraacetate (EDTA) by adding the EDTA to the deionized water; adding a surfactant to the first phase to make a second phase; preparing a colloidal dispersion; adding a particulate colorant to the colloidal dispersion to make a third phase and adding the third phase to the second phase to make a fourth phase; and preparing a wax phase comprising one or more of stearic acid, Caunauba wax, paraffin wax, Candelilla wax or Beeswax to make a wax phase and adding the wax phase to the fourth phase to make a fifth phase; and adding phenoxyethanol and ethylhexylglycerin to the fifth phase to make the gel volume mascara.

DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Inventive embodiments disclosed herein include a gel volume mascara. The gel volume mascara imparts volume and length to lashes. The mascara embodiments disclosed herein are light weight mascara embodiments and have long wearing properties.

One embodiment of the mascara includes the following phases

| | w/w % | Wet Weight (g) |
|---|---|---|
| Phase 1: | | |
| Deionized Water | 53.7000 | 537.0000 |
| Trilon BD | 0.1000 | 1.0000 |
| Phase 2: | | |
| Laponite XLG | 1.5000 | 15.0000 |
| Phase 3: | | |
| Tween 20 | 2.5000 | 25.0000 |
| Phase 4: | | |
| Emulsiphos | 2.5000 | 25.0000 |

-continued

| | w/w % | Wet Weight (g) |
|---|---|---|
| Phase 5: | | |
| Black Iron Oxide C33-5000 | 10.0000 | 100.0000 |
| Orgasol 4000Ex D Nat Cos | 2.0000 | 20.0000 |
| Phase 6: | | |
| Stearic Acid Cos | 1.0000 | 10.0000 |
| Carnauba Wax Prime Yellow 2442 | 6.0000 | 60.0000 |
| Paracera P | 4.8000 | 48.0000 |
| Candelilla Wax 2039Y | 2.0000 | 20.0000 |
| 8104 Kahl White Beeswax | 7.0000 | 70.0000 |
| Euxyl PE 9010 | 0.9000 | 9.0000 |
| DC 749 Fluid | 2.0000 | 20.0000 |
| Phase 7: | | |
| Micromer C60/42 | 3.0000 | 30.0000 |
| Phase 8: | | |
| Sodium Hydroxide-10% | 1.0000 | 10.0000 |

Triton BD, manufactured by BASF, includes disodium ethylenediaminetetraacetate in a concentration of 90% w/w, water in a concentration of 10% w/w and Disodium hydrogen nitrilotriacetate in a concentration of less than 0.12% w/w.

Laponite XLG is a synthetic layered silicate with a low heavy metals content. It is insoluble in water but hydrates and swells to give a clear and colorless colloidal dispersions in water or aqueous solutions of alcohol. At concentrations of 2% or greater in water, highly thixotropic gels are obtained. Once the gels are formed, waxes are added along with colorants into the gel suspension. It is possibly a double colloidal dispersion and the finished product is an emulsion. Laponite XLG is manufactured by Rockwood Additives GmbH, in Moosburg, Del. or by Southern Clay Products, located in Gonzales, Tex.

Tween 20, also known as polysorbate 20 is a polysorbate surfactant whose stability and relative non-toxicity allows it to be used as a detergent and emulsifier. Tween 20 has a chemical formula of $C_{58}H_{114}O_{26}$, a molar mass of 1227.54 g/mol and a density of 1.10 g/cm(3).

Emulsiphos is potassium cetyl phosphate (and) hydrogenated palm glycerides, manufactured by Symrise AG, located in Teterboro, N.J.

Black iron oxide C33-5000 is manufactured by Zauba in Belgium. Other black iron oxide formulations are also suitable such as Black Iron Oxide C33-6000.

Orgasol 4000EX D Nat Cos is a copolyamide 6/12, also called Nylon 6/12. This material is manufactured by Arkema.

Paracera P wax is a paraffin manufactured by fear located worldwide.

Euxyl PE 9010 is phenoxyethanol and ethylhexylglycerin. The material is manufactured by Schulke Inc. and typically acts as a preservative.

Dow Corning (DC) 749 Fluid is a blend of approximately 50 percent high molecular weight resin and 50 percent volatile, low viscosity cyclopentasiloxane.

Micromer C60/42 includes ammonium acrylates copolymer: Proprietary denatured alcohol; 64-17-5; disodium deceth-5-sulfosuccinate; 68630-97.7; Laureth-30: 9002-92-0; sodium dehydroacetate: 4418-26-2 and water: 7732. The Micromer C60/42 is manufactured by aic of Framingham, Mass.

The following is a formulation embodiment disclosing more generic ingredients that are suitable for use. The ingredients are sorted in decreasing order of predominance.

| Ingredient | % w/w |
|---|---|
| Water | 53.70000 |
| Iron Oxides | 10.00000 |
| Beeswax | 7.00000 |
| Cera Carnauba/*Copernicia Cerifera* (Carnauba) Wax/CIRE de Carnauba | 6.00000 |
| Paraffin | 4.80000 |
| Polysorbate 20 | 2.42500 |
| Water | 2.41000 |
| *Euphorbia Cerifera* (Candelilla) Wax | 2.00000 |
| Nylon-6/12 | 2.00000 |
| Lithium Magnesium Sodium Silicate | 1.50000 |
| Potassium Cetyl Phosphate | 1.27500 |
| Hydrogenated Palm Glycerides | 1.22500 |
| Ammonium Acrylates Copolymer | 1.17300 |
| Trimethylsiloxysilicate | 1.00000 |
| Cyclopentasiloxane | 1.00000 |
| Stearic Acid | 1.00000 |
| Phenoxyethanol | 0.80910 |
| Alcohol Denat. | 0.22500 |
| Disodium Deceth-5 Sulfosuccinate | 0.12000 |
| Sodium Hydroxide | 0.10000 |
| Ethylhexylglycerin | 0.09000 |
| Disodium EDTA | 0.09000 |
| Laureth-30 | 0.04500 |
| Sodium Dehydroacetate | 0.01200 |
| Tocpheral | 0.00090 |
| Nitrilotriacetic Acid | |
| MEK | |

Variation of water content in the formulation changes the degree of volumizing. A greater amount of water thins the formulation and reduces volumizing. In some formulation embodiments, one or more of the following ingredients are eliminated: Laponite (synthetic layered silicate), Orgasol 4000EX (Nylon 6/12), DC 749, Micromer C60/42, Sodium Hydroxide, Emulsiphos, along with any of the waxes in Phase 6.

Another super curler gel mascara embodiment is as follows:

| Ingredient | Wet Percent by Wt. |
|---|---|
| Phase 1 | |
| Deionized Water | 46.7% |
| Trilon BD | 0.10 |
| Phase 2 | |
| Laponite XLG | 1.50 |
| Phase 3 | |
| Tween 20 | 2.50 |
| Phase 4 | |
| Emulsiphos | 2.50 |
| Phase 5 | |
| Black Iron Oxide C33-5000 | 3.25 |
| Black Iron Oxide C33-6000 | 6.75 |
| Orgasol 4000EX D Nat Cos | 2.00 |
| Phase 6 | |
| Stearic Acid Cos | 1.00 |
| Carnauba Wax Prime Yellow 2442 | 6.00 |
| Paracerap | 4.80 |
| Candelilla Wax 2039Y | 2.00 |
| 8104 Kahl White Beeswax | 7.00 |
| Phase 7 | |
| DC 749 Fluid | 2.00 |
| Phase 8 | |
| Euxyl PE 9010 | 0.90 |

-continued

| Ingredient | Wet Percent by Wt. |
|---|---|
| Phase 9 | |
| Sodium Hydroxide-10% | 1.00 |
| Phase 10 | |
| Micromer C60/42 | 10.00 |

One other embodiment for a top speed volume mascara is as follows:

| Ingredient | Wet % by wt. |
|---|---|
| Phase 1 | |
| Deioonized Water | 53.7% |
| Trilon BD | 0.10 |
| Phase 2 | |
| Labonite XLG | 1.50 |
| Phase 3 | |
| Tween 20 | 2.50 |
| Phase 4 | |
| Emulsiphos | 2.50 |
| Phase 6 | |
| Black Iron Oxide C33-5000 | 3.25 |
| Black Iron Oxide C33-6000 | 6.75 |
| Orgasol 4000EX D Nat COS | 2.00 |
| Phase 6 | |
| Stearic Acid Cos | 1.00 |
| Carnauba Wax Prime Yellow 2442 | 6.00 |
| Paracerap | 4.80 |
| Candelilla Wax 2039Y | 2.00 |
| 8104 Kahl white Beeswax | 7.00 |
| Phase 7 | |
| DC 749 Fluid | 2.00 |
| Phase 8 | |
| EUXYL PE 9010 | 0.90 |
| Phase 9 | |
| Sodium Hydroxide-10% | 1.00 |
| Phase 10 | |
| Micormer C60/42 | 3.00 |

Embodiments include a mascara comprising:

| Ingredient | % w/w |
|---|---|
| Water | 53.70000 |
| Iron Oxides | 10.00000 |
| Beeswax | 7.00000 |
| Cera Carnauba/*Copernicia Cerifera* (Carnauba) Wax/CIRE de Carnauba | 6.00000 |
| Paraffin | 4.80000 |
| Polysorbate 20 | 2.42500 |
| Water | 2.41000 |
| *Euphorbia Cerifera* (Candelilla) Wax | 2.00000 |
| Nylon-6/12 | 2.00000 |
| Lithium Magnesium Sodium Silicate | 1.50000 |
| Potassium Cetyl Phosphate | 1.27500 |
| Hydrogenated Palm Glycerides | 1.22500 |
| Ammonium Acrylates Copolymer | 1.17300 |
| Trimethylsiloxysilicate | 1.00000 |
| Cyclopentasiloxane | 1.00000 |
| Stearic Acid | 1.00000 |
| Phenoxyethanol | 0.80910 |
| Alcohol Denat. | 0.22500 |
| Disodium Deceth-5 Sulfosuccinate | 0.12000 |
| Sodium Hydroxide | 0.10000 |
| Ethylhexyl glycerin | 0.09000 |
| Disodium EDTA | 0.09000 |
| Laureth-30 | 0.04500 |
| Sodium Dehydroacetate | 0.01200 |
| Tocpheral | 0.00090 |

For some embodiments, the mascara further comprises nitrilotriacetic acid and Methyl Ethyl Ketone.

Another embodiment includes a mascara, comprising:
Water in a concentration of at least about 45% by weight;
Disodium ethylenediaminetetraacetate;
Polysorbate 20;
Black iron oxide;
One or more waxes selected from the group consisting of beeswax, Cera Carnauba/*Copernicia Cerifera* (Carnauba) Wax/CIRE de Carnauba, and paraffin in a concentration of 15-20% by weight; and
A synthetic layered silicate, insoluble in water, in a concentration effective for forming a colloidal dispersion with the water.

A method of making a gel volume mascara, comprising:
Preparing a first phase of deionized water and ethylenediaminetetraacetate (EDTA) by adding the EDTA to the deionized water;
Adding a surfactant to the first phase to make a second phase;
Preparing a colloidal dispersion;
Adding a particulate colorant to the colloidal dispersion to make a third phase and adding the third phase to the second phase to make a fourth phase; and
Preparing a wax phase comprising one or more of stearic acid, Caunauba wax, paraffin wax, Candelilla wax or Beeswax to make a wax phase and adding the wax phase to the third phase to make a fifth phase; and adding phenoxyethanol and ethylhexylglycerin to the fifth phase to make the gel volume mascara.

For some embodiments, the method further comprises adding a phase to the first phase of deionized water and EDTA that comprises a synthetic layered silicate with low heavy metals content.

For some embodiments, the method further comprises potassium cetyl phosphate and hydrogenated palm glycerides, added to the second phase.

It will be readily understood to those skilled in the art that various other changes in the details, material, and arrangements of the parts and method stages which have been described and illustrated in order to explain the nature of this inventive subject matter may be made without departing from the principles and scope of the inventive subject matter as expressed in the subjoined claims.

What is claimed is:
1. A gel mascara, comprising:
deionized water in a concentration of at least about 45%;
black iron oxide;
synthetic layered silicate in a concentration effective for forming a colloidal dispersion with the water;
disodium EDTA;
polysorbate 20;
potassium cetyl phosphate and hydrogenated palm glycerides in a blend;

one or more of Carnauba Wax, paraffin, Candelilla Wax and White Beeswax in a concentration range of 1.5 to 20% by weight and ammonium acrylate copolymer.

2. A mascara, comprising:

deionized water in a concentration of 53.7%;

black iron oxide in a concentration of 10.0% by weight;

synthetic layered silicate in a concentration of 1.5% by weight;

disodium EDTA in a concentration of 0.10% by weight;

polysorbate 20 in a concentration of 2.50% by weight;

potassium cetyl phosphate and hydrogenated palm glycerides in a concentration of 2.5% by weight;

one or more of Carnauba Wax, paraffin, Candelilla Wax and White Beeswax in a concentration range of 2.0% to 20% by weight; and ammonium acrylate copolymer in a concentration of 3.0% by weight.

3. The mascara of claim 1, further comprising nitrilotriacetate.

4. The mascara of claim 1, further comprising methyl ethyl ketone.

5. The mascara of claim 2, further comprising nitrilotriacetate.

6. The mascara of claim 2, further comprising methyl ethyl ketone.

7. The mascara of claim 1, wherein the deionized water, EDTA and synthetic layered silicate comprise a phase.

* * * * *